United States Patent [19]
Guempelein et al.

[11] Patent Number: 5,535,033
[45] Date of Patent: Jul. 9, 1996

[54] CONTACTLESS DATA TRANSMISSION DEVICE

[75] Inventors: Reinhold Guempelein, Leutershausen; Gerhard Roehrlein, Hoechstadt, both of Germany

[73] Assignee: Siemens Aktiengesellschaft, Munich, Germany

[21] Appl. No.: 353,690

[22] Filed: Dec. 12, 1994

[30] Foreign Application Priority Data

Dec. 15, 1993 [DE] Germany ............ 43 42 778.2

[51] Int. Cl.⁶ .................................................. H04B 10/12
[52] U.S. Cl. ........................................................ 359/144
[58] Field of Search ................. 359/144; 340/870.28

[56] References Cited

U.S. PATENT DOCUMENTS

| | | | |
|---|---|---|---|
| 4,002,917 | 1/1977 | Mayo | 250/445 T |
| 4,555,631 | 11/1985 | Martens | 359/159 |
| 4,646,086 | 2/1987 | Helzel | 359/159 |
| 4,992,941 | 2/1991 | Bruening et al. | 364/413.15 |
| 4,996,435 | 2/1991 | Keller | 359/144 |
| 5,229,871 | 7/1993 | Czarnek | 359/154 |

FOREIGN PATENT DOCUMENTS

| | | | |
|---|---|---|---|
| 2237695 | 2/1974 | Germany | 359/144 |
| 2441359 | 3/1976 | Germany | 359/144 |
| 3326661 | 1/1985 | Germany | 359/144 |
| 3908697 | 3/1991 | Germany | |
| 0158744 | 8/1985 | Japan | 359/144 |
| 0216268 | 10/1985 | Japan | 359/144 |
| 0547813 | 2/1977 | U.S.S.R. | 359/144 |
| 0964697 | 10/1982 | U.S.S.R. | 359/144 |
| 2074313 | 10/1981 | United Kingdom | 359/144 |
| 2169464 | 7/1986 | United Kingdom | 359/144 |

OTHER PUBLICATIONS

"Illumination of Architecture and Landscape with Plastic Optical Fibre," Ono, Papers Presented at POF '93, The Second Annual Conference (Jun., 1993), pp. 71–74.

*Primary Examiner*—Leslie Pascal
*Attorney, Agent, or Firm*—Hill, Steadman & Simpson

[57] ABSTRACT

A contactless data transmission system includes a laterally emitting optical conductor connected to an electro-optical data transmitter. The optical conductor is formed by a bundle of optical fibers provided with a transparent cladding, so that the optical conductor laterally emits signals along its entire length corresponding to the data signals which are coupled into the optical conductor. An opto-electrical detector is disposed at a location next to the optical conductor, for receiving the laterally emitted optical signals therefrom. The optical conductor and its data source, and the detector, can be respectively mounted on parts of a system which are relatively movable with respect to each other, such as the stationary frame and the rotating ring of a computer tomography apparatus.

5 Claims, 2 Drawing Sheets

5,535,033

CONTACTLESS DATA TRANSMISSION DEVICE

BACKGROUND OF THE INVENTION

1. Field of the Invention

The present invention is directed to a device for transmitting data in a contact-free manner between a data transmitter and a data receiver, and in particular to such a device suitable for use in transmitting data between a rotating part and a stationary part of a computed tomography apparatus.

2. Description of the Prior Art

Computed tomography systems are known in the art having a rotating part, which usually carries an x-ray source and a detector, and a stationary part, such as a frame, on which the rotating part is mounted. Electrical connections to the circuitry for processing the detector signals are attached to the stationary part, and it is therefore necessary to transmit data from the rotating part to the stationary part. In view of the relative rotation between the rotating part and the stationary part, the data connection cannot be permanent, i.e., hard-wired, otherwise the relative movement between the two parts will be impeded.

Heretofore, electro-mechanical structures, such as wiper rings and contact brushes, as well as optical means, such as light-emitting diodes, have been used to transmit signals between the rotating part and the stationary part in such known systems. In such known solutions, it is necessary to employ a number of receivers arranged successively around the transmitting part, so that one receiver at a time can receive data from a transmitter carried by the rotating part as the data transmitter rotates by the respective receiver.

It is also known employ transmitters which couple a signal into a divided waveguide, with the division of the waveguide being such that the two halves thereof are movable relative to each other, with the incoming signal being forwarded to a reception location. In the general field of signal transmission, it is known to couple a digital signal into an optical fiber, with the fiber being mechanically worked so that light emerges from the fiber laterally, and can be detected by a suitable receiver or reception element.

SUMMARY OF THE INVENTION

It is an object of the present invention to provide a contactless data transmission device which permits data to be transmitted between system components which are movable relative to each other, in a manner which achieves a continuous data connection, and which is constructed in a simple way and which is immune from interference.

The above objects are achieved in accordance with the principles of the present invention in an apparatus having a stationary part and a movable part, with a contactless data transmission device being formed by at least one laterally emitting optical conductor, to which an electro-optical data transmitter is coupled at one end face, with an opto-electrical detector (transducer) being disposed at a side of the optical conductor so as to receive the laterally emitted signals therefrom. The optical conductor is carried at one of the rotating or stationary parts, and the opto-electrical detector is carried at the other part.

The optical conductor may be formed by a bundle of individual optical fibers, having a transparent cladding. Optical fibers of this type which are known to those skilled in the art can be employed in the invention as the optical conductor. Given a feed of sufficient optical power to the end face of the bundle at which the transmitter is disposed, a uniform lateral emission of optical power along a bundle length of up to 60 meters can be achieved.

DESCRIPTION OF THE PREFERRED EMBODIMENTS

Figure 1:
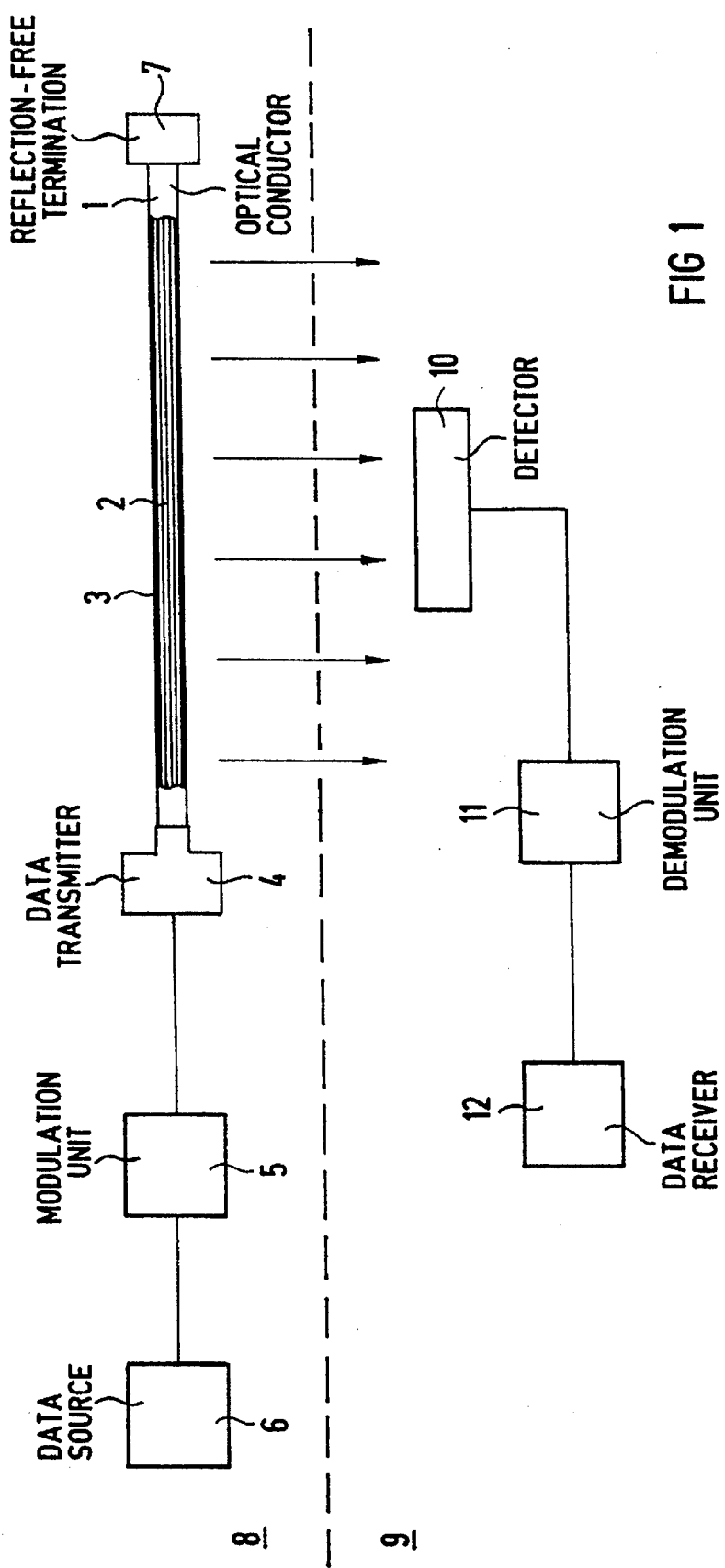
FIG. 1 is a block diagram of a contactless data transmission system constructed in accordance with the principles of the present invention.

The contactless data transmission system constructed in accordance with the principles of the present invention which is shown in FIG. 1 includes an optical conductor 1 which is composed of a bundle of individual optical fibers 2, and which is provided with a transparent cladding 3. A data transmitter 4, formed by an electro-optical transducer, is optically connected to one end face of the optical conductor 1. The light emitted by the data transmitter 4 consists of signals generated electrically by a data source 6, and modulated in a modulation unit 5, before conversion into optical signals in the data transmitter 4. The optical conductor 1 has a reflection-free termination 7 disposed at an opposite end thereof.

The aforementioned components, in combination, form a transmission arrangement 8. A receiver arrangement 9 is formed by a detector 10, in the form of a opto-electrical transducer, a demodulation unit 11, and a data receiver 12.

The information to be transmitted is coupled into the optical conductor 1 in the form of light pulses. These pulses propagate in the entire optical conductor 1, causing lateral optical power to be emitted over the entire length of the optical conductor 1. This laterally emitted optical power is modulated, and conforms to the signal from the data source 6 modulated by the modulator unit 5. The laterally emitted optical power can be detected by one or more reception elements, however, a single detector 10 can be used, which can be moved along the optical conductor 1, since the optical conductor 1 laterally emits a signal at each location along its entire length. The contactless data transmission system is therefore suitable for transmitting data between a stationary part and a rotating part, with the transmission arrangement 8 being mounted on the stationary part, and the receiver arrangement 9 being mounted on the rotating part, for example. The system is suitable, however, for transmitting data in a non-contacting fashion between any relatively movable locations.

Figure 2:
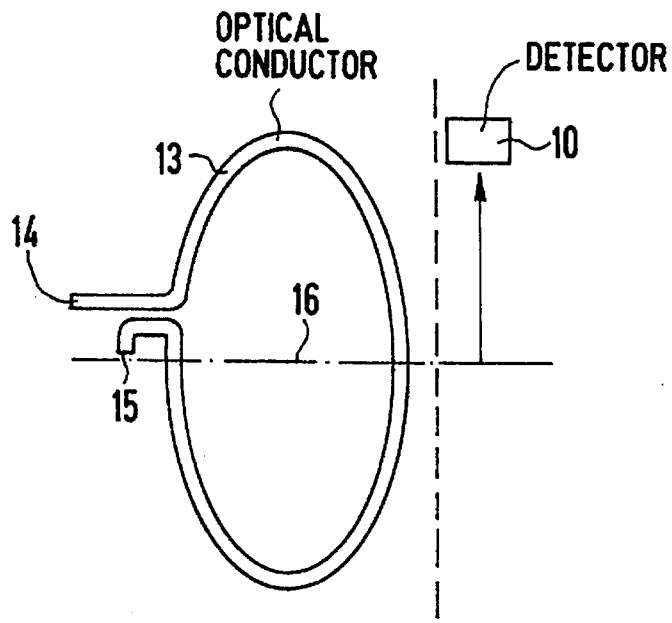
FIG. 2 shows a further embodiment of the data transmission system of FIG. 1.

The embodiment shown in FIG. 2 is particularly suitable for employment in a computed tomography apparatus. As noted above, such systems commonly employ a rotating part and a stationary part. Examples of such computed tomography systems are disclosed in U.S. Pat. No. 4,992,941 and U.S. Pat. No. 4,002,917, the teachings of which are incorporated herein by reference. In the embodiment of FIG. 2, a circular, open optical conductor 13 is provided which is coupled to the data transmitter 4 at an end 14, and is coupled to the reflection-free termination 7 at an end 15. The detector 10 is oriented laterally next to the optical conductor 13. The part disposed to the left of the dashed line in FIG. 2 rotates around an axis 16, whereas the part disposed to the right of the dashed line is stationary.

Figure 3:
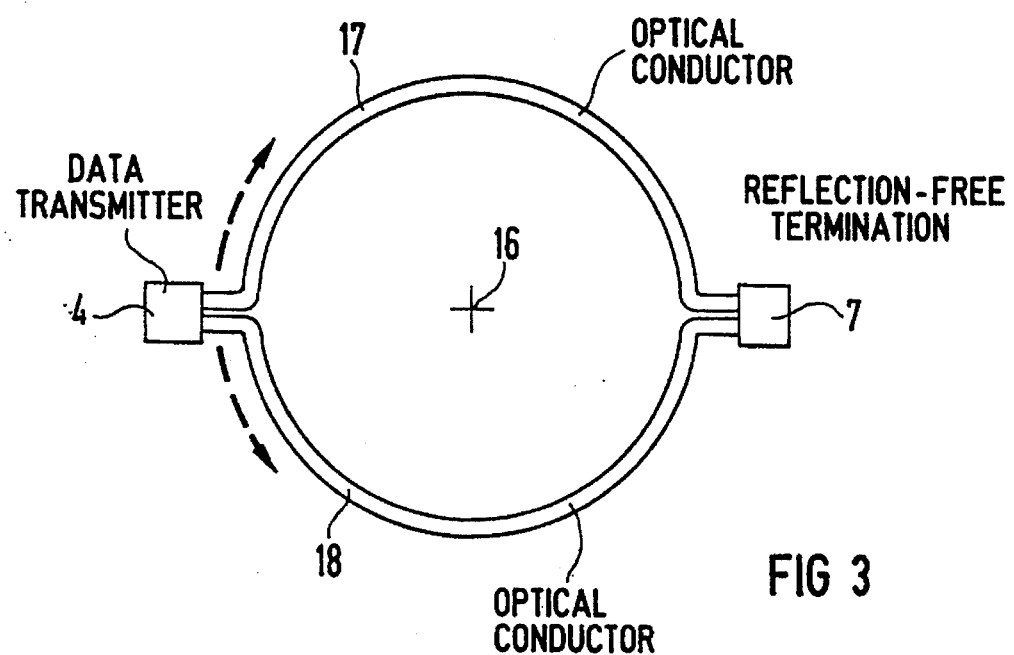
FIG. 3 shows another embodiment of the data transmission system of FIG. 1.

In the embodiment of FIG. 3, two semicircular optical conductors 17 and 18 are arranged to form a circle, and are each coupled at one end to a common data transmitter 4, and are each coupled to a common, reflection-free termination 7 at their other ends. The infeed locations for the data are disposed side-by-side, so that the signal propagates opposite to the rotational direction in one of the optical fibers 17 or 18, and propagates in same direction as the rotation in the other of the optical conductors 17 and 18. No discontinuity in transit time arises due to the rotation.

The embodiments of FIGS. 2 and 3 are particularly suitable for employment in a computed tomography apparatus for the transmission of the data between the rotating part and the stationary part.

The embodiments described herein require no complicated working of the optical fibers and have a simple structure, because standard components are employed, and are suitable for the transmission of high data rates.

Although modifications and changes may be suggested by those skilled in the art, it is the intention of the inventors to embody within the patent warranted hereon all changes and modifications as reasonably and properly come within the scope of their contribution to the art.

We claim as our invention:

1. A contactless data transmission system comprising:

first and second system parts which are relatively movable with respect to each other;

an optical conductor and an electro-optical data transmitter coupled at one end of said optical conductor, disposed on one of said parts, said optical conductor being formed by a bundle of optical fibers and having a transparent cladding for laterally emitting an optical signal;

said optical conductor comprising a first semicircular optical conductor and second semicircular optical conductor, said first and second semicircular optical conductors being oriented to form a circle, and each semicircular optical conductor having a first end connected to a common data transmitter, and an opposite end connected to a common, reflection-free termination; and an opto-electrical detector disposed at the other of said relatively movable parts for receiving the laterally emitted signals from said optical conductor.

2. A contactless data transmission system as claimed in claim 1 wherein said optical conductor comprises a circular optical conductor loop having a first end coupled to said data transmitter, and a second end coupled to a reflection-free termination.

3. A contactless data transmission system as claimed in claim 1 wherein said system part at which said optical conductor is disposed is rotatable relative to said system part at which said detector is disposed.

4. A contactless data transmission system as claimed in claim 3 wherein said system part at which said optical conductor is disposed consists of a rotating part in a computer tomography apparatus, and wherein said system part at which said detector is disposed consists of a stationary part of said computer tomography apparatus.

5. A method for transmitting data between a stationary part and a rotating part in a computer tomography apparatus comprising:

providing first and second semicircular, laterally emitting optical conductors each having an input end and each terminating in a reflection-free termination;

arranging said optical conductors in a circle on said stationary part;

generating electrical signals to be transmitted and converting said electrical signals into optical signals;

coupling said optical signals into said optical conductors so that said optical conductors laterally emit said optical signals; and rotating an opto-electrical detector around said circle formed by said optical conductors to receive said optical signals laterally emitted by said optical conductors.

\* \* \* \* \*